United States Patent
Mudaliar et al.

(10) Patent No.: US 11,440,890 B2
(45) Date of Patent: Sep. 13, 2022

(54) MANUFACTURING PROCESS FOR 2-NITROIMINO HETEROCYCLIC COMPOUNDS

(71) Applicant: UPL LTD, Haldia (IN)

(72) Inventors: Chandrasekhar Dayal Mudaliar, Mumbai (IN); Sadanand Sadashiv Pandit, Mumbai (IN); Jaidev Rajnikant Shroff, Dubai (AE); Vikram Rajnikant Shroff, Dubai (AE)

(73) Assignee: UPL LTD., Haldia (IN)

( * ) Notice: Subject to any disclaimer, the term of this patent is extended or adjusted under 35 U.S.C. 154(b) by 0 days.

(21) Appl. No.: 17/272,712

(22) PCT Filed: Sep. 11, 2019

(86) PCT No.: PCT/IB2019/057642
§ 371 (c)(1),
(2) Date: Mar. 2, 2021

(87) PCT Pub. No.: WO2020/058807
PCT Pub. Date: Mar. 26, 2020

(65) Prior Publication Data
US 2021/0214313 A1 Jul. 15, 2021

(30) Foreign Application Priority Data
Sep. 17, 2018 (IN) .............................. 201831035021

(51) Int. Cl.
*C07D 233/52* (2006.01)
*C07D 239/12* (2006.01)
*C07D 401/06* (2006.01)

(52) U.S. Cl.
CPC ......... *C07D 233/52* (2013.01); *C07D 239/12* (2013.01); *C07D 401/06* (2013.01)

(58) Field of Classification Search
CPC ... C07D 233/52; C07D 239/12; C07D 401/06
See application file for complete search history.

(56) References Cited

U.S. PATENT DOCUMENTS

| | | |
|---|---|---|
| 5,453,529 A | 9/1995 | Kojima et al. |
| 9,212,162 B1 | 12/2015 | Bristow et al. |

FOREIGN PATENT DOCUMENTS

| | | | |
|---|---|---|---|
| CN | 104672212 A | * | 6/2015 |
| CN | 105924428 A | | 9/2016 |
| CN | 107235970 A | | 10/2017 |
| CN | 107445897 A | | 12/2017 |

OTHER PUBLICATIONS

Wu et al., Machine Translation of CN 10467212A, 2015.*
Wu et al., CASREACT Abstract 163:93098 (2015).*
International Search Report and Written Opinion for International Application PCT/IB2019/057642 International Filing Date: Sep. 11, 2019; dated Dec. 18, 2019; 13 pages.

* cited by examiner

*Primary Examiner* — Deepak R Rao
(74) *Attorney, Agent, or Firm* — Cantor Colburn LLP

(57) ABSTRACT

The present invention relates to a process for manufacture of 2-nitroimino heterocyclic compounds and intermediates thereof. More particularly, the present invention relates to a convenient manufacturing process for preparation of 2-nitroimino imidazolidine compounds.

14 Claims, No Drawings

MANUFACTURING PROCESS FOR 2-NITROIMINO HETEROCYCLIC COMPOUNDS

CROSS REFERENCE TO RELATED APPLICATIONS

This application is a National Stage application of PCT/IB2019/057642, filed Sep. 11, 2019, which claims the benefit of priority to Indian Patent Application No. 201831035021, filed Sep. 17, 2018, both of which are incorporated by reference in their entirety herein.

FIELD OF THE INVENTION

The present invention relates to a process for manufacture of 2-nitroimino heterocyclic compounds and intermediates thereof. More particularly, the present invention relates to a convenient manufacturing process for preparation of 2-nitroimino imidazolidine compounds.

BACKGROUND OF THE INVENTION

Nitroimino heterocyclic compounds of general Formula A are useful intermediates for certain insecticides and for products with certain medicinal applications. Imidacloprid is one such widely used insecticide.

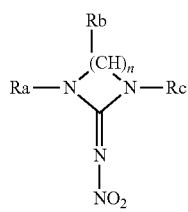

Formula A wherein $R_a$, $R_b$ and $R_c$ are the same or different and represent hydrogen or a lower alkyl of 1 to 4 carbon atoms, optionally substituted with a heterocyclic ring wherein one of the ring atoms comprises nitrogen, and wherein said ring is being optionally substituted with halogen or lower alkyl of 1 to 4 carbon atoms, and n is 2, 3 or 4.

Imidacloprid is a systemic insecticide with translaminar activity and with contact and stomach action. It is widely used for controlling of sucking insects, including rice-, leaf- and plant hoppers, aphids, thrips and whitefly. It is also found to be effective against soil insects, termites and some species of biting insects, such as Rice water weevil and Colorado beetle. Imidacloprid finds use as a seed dressing, as soil treatment and as foliar treatment in different crops, e.g. rice, cotton, cereals, maize, sugar beet, potatoes, vegetables, citrus fruit, pome fruit and stone fruit.

Nitroguanidine of Formula II has been identified as an important intermediate for the preparation of insecticide imidacloprid.

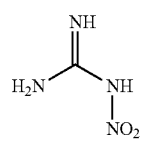

Formula II

Compound of Formula II is categorized as shock sensitive material which may decompose violently if struck or heated. Considering the importance of the intermediate, it requires exceptional care while manufacturing the compound. Handling and storage of such a compound requires controlled environments.

CN107445897 discloses a process for preparing nitroimino imidazolidine starting from guanidine nitrate. The disclosed process is a two-step process wherein the first step involves the preparation of nitroguanidine from guanidine nitrate and in the second step, nitroguanidine is converted to 2-nitroimino imidazolidine using tetrabutylammonium bromide as a catalyst. The process involves the isolation of nitoguanidine which will result in acidic effluent in large quantities.

U.S. Pat. No. 5,453,529 discloses a process for preparation of nitroimino compounds of general Formula B, as intermediate for insecticides and pharmaceuticals starting from imidodithiocarbonate.

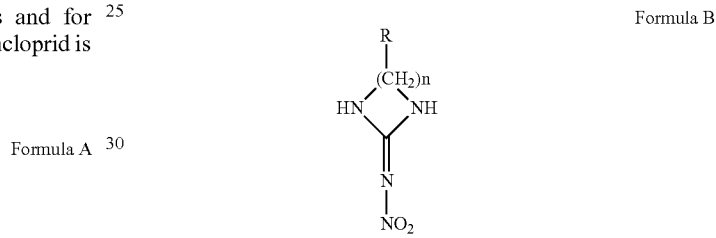

Formula B

Therefore, there is need in art to develop novel and convenient process for preparation of nitroimino heterocyclic compounds. Inventors of the present invention developed a process for the preparation of nitroimino heterocyclic compound of Formula B wherein the process avoids the isolation of shock sensitive compound of Formula II. The process further minimizes effluent generation considerably. Further, there is provided a process for preparation of imidacloprid using this intermediate compound.

OBJECTS OF THE INVENTION

It is an object of the present invention to provide a process for the preparation of nitroimino heterocyclic compounds.

Another object of the present invention is to provide a one pot process for the preparation of nitroimino heterocyclic compounds wherein isolation of intermediate compound of Formula II is avoided.

Yet another object of the present invention is to provide simple and an environmentally friendly process for the preparation of nitroimino heterocyclic compounds wherein effluent generation is minimized.

Another object of the present invention is to provide a process for preparing Imidacloprid.

SUMMARY OF THE INVENTION

The present invention provides a process for preparing nitroimino heterocyclic compounds of Formula B:

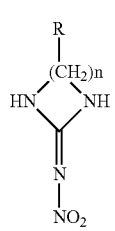

Formula B said process comprising reacting a compound of Formula II:

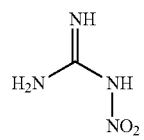

Formula II with a diamine of Formula III

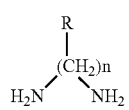

Formula III wherein said compound of formula II is reacted with said compound of formula III without isolating or separating it from a mixture comprising the reaction product of a reaction of a compound of formula I with an acid:

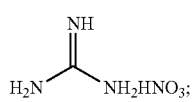

Formula I wherein R represent hydrogen or an optionally substituted lower alkyl of 1 to 4 carbon atoms; and n is 2, 3 or 4.

The present invention provides a process for preparing nitroimino heterocyclic compounds of Formula B in a one pot, said process comprising:

a) reacting a compound of Formula I with an acid to give a compound of Formula II; and

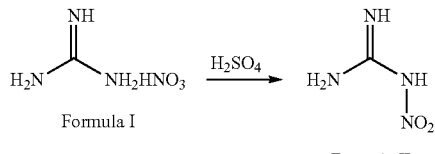

b) reacting a compound of Formula II with a diamine of Formula III to give a compound of Formula B, wherein compound of formula II is not isolated,

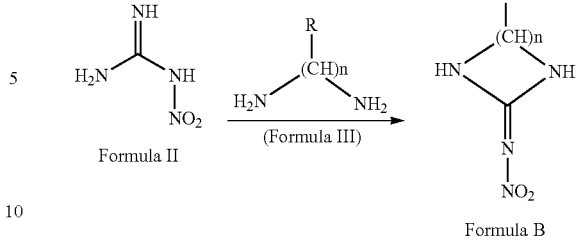

Formula B and wherein R represent hydrogen or an optionally substituted lower alkyl of 1 to 4 carbon atoms and n is 2, 3 or 4.

The present invention provides a process for preparing nitroimino heterocyclic compounds of Formula IV:

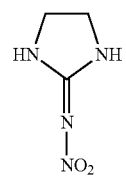

Formula IV said process comprising reacting a compound of Formula II with ethylene diamine:

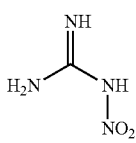

Formula II wherein said compound of formula II is reacted with ethylene diamine without isolating or separating the compound of formula II from a mixture comprising the reaction product of a reaction of a compound of formula I with an acid:

Formula I $H_2N-C(=NH)-NH_2 \cdot HNO_3$.

The present invention further provides a process for preparing compound of Formula IV in a one pot, said process comprising:

a) reaction of compound of Formula I with sulfuric acid to give a compound of Formula II; and

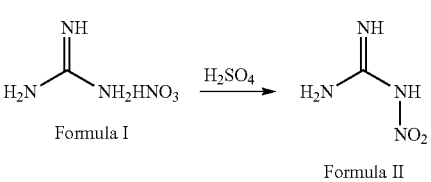

b) reaction of compound of Formula II with ethylene diamine to give a compound of Formula IV, wherein compound of Formula II is not isolated.

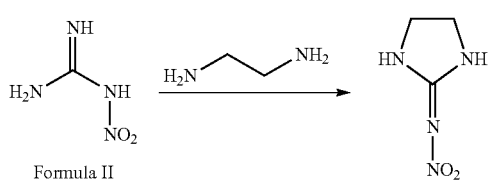

Formula II → Formula IV

The present invention provides a process for preparing imidacloprid, said process comprising reacting a compound of Formula IV with a compound of Formula V to obtain imidacloprid;

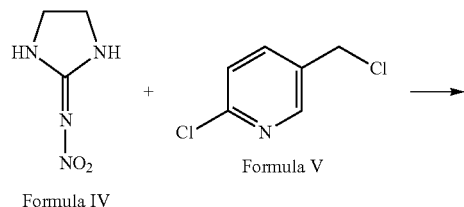

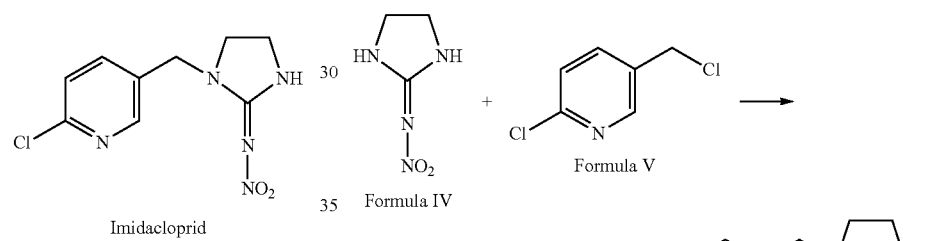

Imidacloprid wherein said compound of formula IV is prepared by a process comprising reacting a compound of Formula II with ethylene diamine:

Formula II wherein said compound of formula II is reacted with ethylene diamine without isolating or separating the compound of Formula II from a mixture comprising the reaction product of a reaction of a compound of formula I with an acid:

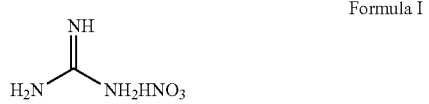

Formula I

The present invention provides a process for preparing imidacloprid, said process comprising:

a) reaction of compound of Formula I with sulfuric acid to give a compound of Formula II;

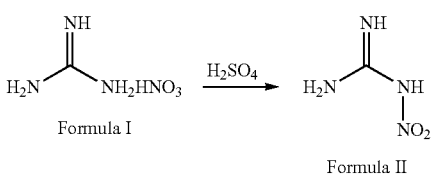

b) reaction of compound of Formula II with ethylene diamine to give a compound of Formula IV, wherein compound of formula II is not isolated;

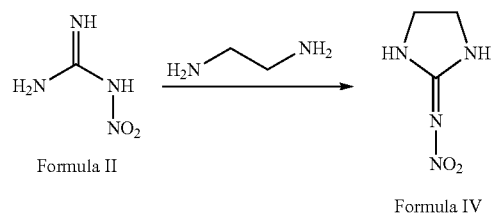

c) reaction of compound of Formula IV with compound of Formula V to obtain imidacloprid Imidacloprid

DETAILED DESCRIPTION OF THE INVENTION

The present invention provides an economical and environmentally friendly process for the preparation nitroimino heterocyclic compounds. In an embodiment, the present invention demonstrates the synthesis by a one pot process for the preparation of 2-nitroimino heterocyclic compounds such as 2-nitroimino imidazolidine. 2-nitroimino imidazolidine prepared by the present process is further used for the manufacture of insecticide Imidacloprid.

In an embodiment, the one pot process can involve one or more steps. However, the products of each step do not have to be isolated or purified between steps and all of the steps can take place in one reactor.

Throughout the specification guanidine nitrate is represented by Formula I, nitroguanidine is represented by Formula II, 2-nitroimino imidazolidine is represented by Formula IV and 2-chloro-5-(chloromethyl)pyridine is represented by Formula V.

In any aspect or embodiment described hereinbelow, the phrase comprising may be replaced by the phrases "consisting of" or "consisting essentially of" or "consisting substantially of". In these aspects or embodiment, the combination or composition described includes or comprises or consists of or consists essentially of or consists substantially of the specific components recited therein, to the exclusion of other fungicides or insecticide or herbicides or plant growth promoting agents or adjuvants or excipients not specifically recited therein.

In an aspect, the present invention provides a process for preparing nitroimino heterocyclic compounds of Formula B:

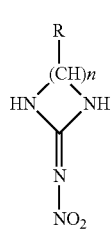

Formula B said process comprising reacting a compound of Formula II:

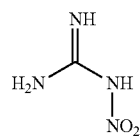

Formula II with a diamine of Formula III

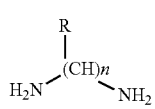

Formula III wherein said compound of formula II is reacted with said compound of formula III without isolating or separating it from a mixture comprising the reaction product of a reaction of a compound of formula I with an acid:

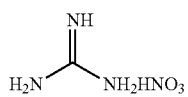

Formula I wherein R represent hydrogen or an optionally substituted lower alkyl of 1 to 4 carbon atoms; and n is 2, 3 or 4.

In an embodiment, the process for the preparation of the compound B is a one-pot process.

Thus in an embodiment, the present invention provides a process for preparing nitroimino heterocyclic compounds of Formula B in a one pot said process comprising:

a) reaction of compound of Formula I with sulfuric acid to give a compound of Formula II, and

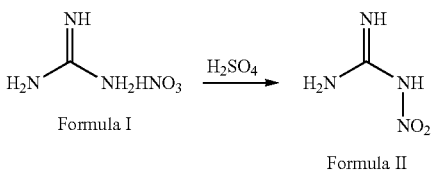

b) reaction of compound of Formula II with a diamine of Formula III to give a compound of Formula B, wherein compound of formula II is not isolated,

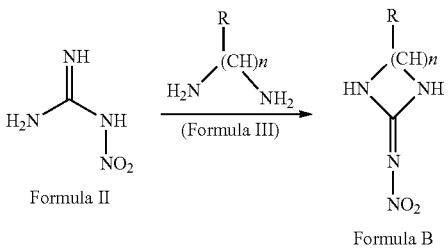

wherein R represent hydrogen or an optionally substituted lower alkyl of 1 to 4 carbon atoms and n is 2, 3 or 4.

In an embodiment R is hydrogen and n is 2.

In another embodiment R is hydrogen and n is 3.

In another embodiment, the substitution on lower alkyl group may include optionally substituted alkyl, aralkyl or heteroaralkyl groups.

In an embodiment, the heteroatom is nitrogen.

In another embodiment alkyl, aralkyl or heteroaralkyl groups are substituted with halogen or haloalkanes.

In an embodiment, the acid is sulfuric acid.

In an embodiment of the present invention, formula I and sulfuric acid is present in an amount from about 1:1 to about 1:5 parts by weight.

In an embodiment of the present invention, formula I and sulfuric acid is present in an amount from about 1:1 to about 1:3 parts by weight.

In an embodiment, step (a) is carried out at a temperature in the range of about of 5° C. to about 50° C.

In an embodiment, step (b) is carried out at a temperature in the range of about 5° C. to about 50° C.

In an embodiment, the compound of formula B is selected from

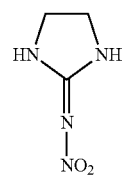

Formula IV

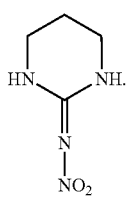

Formula VI

In an embodiment the compound of formula B is compound of formula IV.

In an aspect, the present invention provides a process for preparing nitroimino heterocyclic compounds of Formula IV:

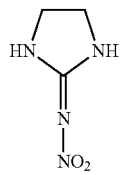

Formula IV said process comprising reacting a compound of Formula II with ethylene diamine:

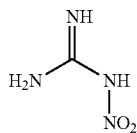

Formula II wherein said compound of formula II is reacted with ethylene diamine without isolating or separating it from a mixture comprising the reaction product of a reaction of a compound of formula I with an acid:

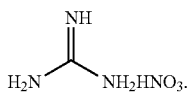

Formula I

In an embodiment, the acid is sulfuric acid.

In an embodiment, this process for the preparation of compound of formula IV is a one-pot process.

In this embodiment, there is provided a process for preparing compound of Formula IV in a one pot, said process comprising:

a) reaction of compound of Formula I with sulfuric acid to give a compound of Formula II; and

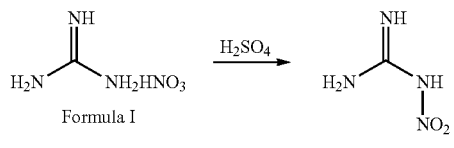

b) reaction of compound of Formula II with ethylene diamine to give a compound of Formula IV, wherein compound of Formula II is not isolated

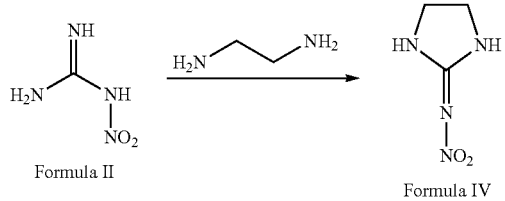

In an embodiment, the compound of formula IV prepared by the process of the present invention is substantially free of the compound of formula II.

The term substantially free of, as used herein, is intended to denote the presence of the impurity compound being in an amount less than 3%, preferably less than 1%, more preferably less than or about 0.5%, preferably less than, or about, 0.25% and most preferably less than or about 0.1% of the target compound.

In an embodiment, the present invention provides a compound IV being substantially free of the compound of formula II.

In an embodiment, the present invention provides a compound IV having less than 3% by weight of the compound of formula II.

In an embodiment, the present invention provides a compound IV having less than 1% by weight of the compound of formula II.

In an embodiment, the present invention provides a compound IV having less than, or about, 0.5% by weight of the compound of formula II.

In an embodiment, the present invention provides a compound IV having less than, or about, 0.25% by weight of the compound of formula II.

In an embodiment, the present invention provides a compound IV having less than, or about, 0.1% by weight of the compound of formula II.

In an embodiment of the present invention, formula I and sulfuric acid is present in an amount from about 1:1 to about 1:5 parts by weight.

In an embodiment of the present invention, formula I and sulfuric acid is present in an amount from about 1:1 to about 1:3 parts by weight.

In an embodiment, step (a) is carried out at a temperature in the range of about 5° C. to about 50° C.

In an embodiment, step (a) reaction mass is neutralized by mixing with aqueous ammonia solution.

In another embodiment, step (a) reaction mass is added to aqueous ammonia solution to effect neutralization.

In an embodiment, step (b) is carried out at a temperature in the range of about 5° C. to about 50° C.

In another embodiment, there is provided a process for preparing compound of Formula VI in a one pot, said process comprising:

a) reaction of compound of Formula I with sulfuric acid to give a compound of Formula II; and

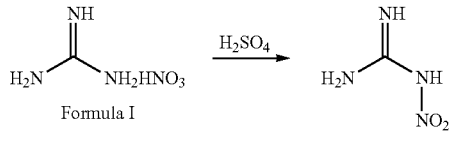

b) reaction of compound of Formula II with propylene diamine to give a compound of Formula VI, wherein compound of Formula II is not isolated

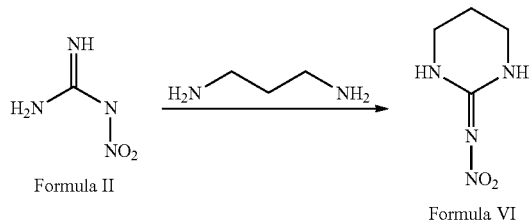 [SMILES: N=C(N)N[N+](=O)[O-] ; NCCCN ; O=[N+]([O-])N=C1NCCCN1]

Formula II → Formula VI

In an embodiment, the compound of formula VI prepared by the process of the present invention is substantially free of the compound of formula II.

In another embodiment, the compound of formula VI was prepared by one pot process without isolating the compound of formula II.

In an aspect, the present invention provides a process for preparing imidacloprid, said process comprising reacting a compound of Formula IV with a compound of Formula V to obtain imidacloprid;

Formula IV + Formula V → Imidacloprid wherein said compound of formula IV is prepared by a process comprising reacting a compound of Formula II with ethylene diamine:

Formula II wherein said compound of formula II is reacted with ethylene diamine without isolating or separating it from a mixture comprising the reaction product of a reaction of a compound of formula I with an acid:

Formula I

In an embodiment, the acid is sulfuric acid.

In an embodiment, the process for preparing the compound of formula IV is a one-pot process.

Thus, in an embodiment, the present invention further provides a process for preparing Imidacloprid, said process comprising:

a) reaction of compound of Formula I with sulfuric acid to give a compound of Formula II;

Formula I → Formula II b) reaction of compound of Formula II with ethylene diamine to give a compound of Formula IV, wherein compound of Formula II is not isolated;

Formula II → Formula IV c) reaction of compound of formula IV with Formula V to give Imidacloprid.

Formula IV + Formula V → Imidacloprid

In an embodiment step (c) is conducted after isolation of compound of Formula IV.

In another embodiment, step (c) is conducted without isolation of compound of Formula IV.

Thus, in an embodiment the present invention, the process of preparing imidacloprid is performed in a one pot.

Further, in an embodiment, there is provided a one pot process for preparing imidacloprid, said process comprising:

a) reaction of compound of Formula I with sulfuric acid to give a compound of Formula II;

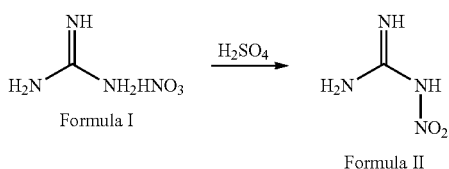

Formula I → Formula II b) reaction of compound of Formula II with ethylene diamine to give a compound of Formula IV, wherein compound of Formula II is not isolated;

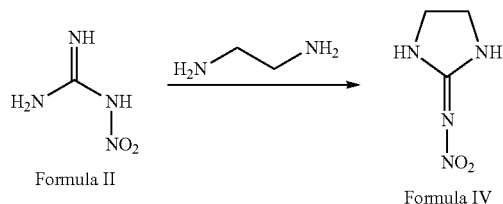

Formula II → Formula IV c) reaction of compound of Formula IV with compound of Formula V to give Imidacloprid

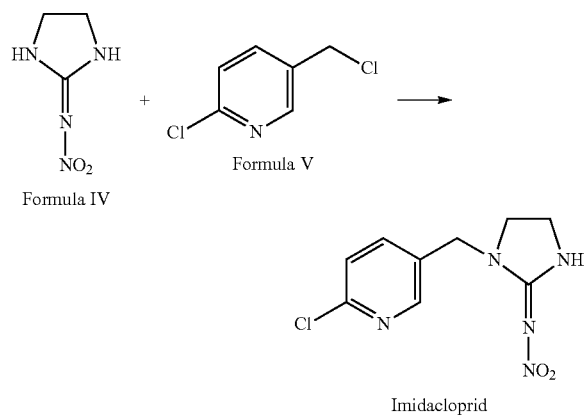

Formula IV + Formula V → Imidacloprid

In an embodiment, the compound imidacloprid prepared by the process of the present invention is substantially free of the compound of formula IV.

The term substantially free of, as used herein, is intended to denote the presence of the impurity compound being in an amount less than 3%, preferably less than 1%, more preferably less than or about 0.5%, and most preferably less than or about 0.1% of the target compound.

In an embodiment, the present invention provides imidacloprid being substantially free of the compound of formula IV.

In an embodiment, the present invention provides imidacloprid having less than 3% by weight of the compound of formula IV.

In an embodiment, the present invention provides imidacloprid having less than 1% by weight of the compound of formula IV.

In an embodiment, the present invention provides imidacloprid having less than, or about, 0.5% by weight of the compound of formula IV.

In an embodiment, the present invention provides imidacloprid having less than, or about, 0.25% by weight of the compound of formula IV.

In an embodiment, the present invention provides imidacloprid having less than, or about, 0.1% by weight of the compound of formula IV.

In an embodiment, the compound imidacloprid prepared by the process of the present invention is substantially free of the compound of formula II.

The term substantially free of, as used herein, is intended to denote the presence of the impurity compound II being in an amount less than 3%, preferably less than 1%, more preferably less than or about 0.5%, and most preferably less than or about 0.1% of the target compound.

In an embodiment, the present invention provides imidacloprid being substantially free of the compound of formula II.

In an embodiment, the present invention provides imidacloprid having less than 3% by weight of the compound of formula II.

In an embodiment, the present invention provides imidacloprid having less than 1% by weight of the compound of formula II.

In an embodiment, the present invention provides imidacloprid having less than, or about, 0.5% by weight of the compound of formula II.

In an embodiment, the present invention provides imidacloprid having less than, or about, 0.25% by weight of the compound of formula II.

In an embodiment, the present invention provides imidacloprid having less than, or about, 0.1% by weight of the compound of formula II.

In an embodiment of the present invention, formula I and sulfuric acid is present in an amount from about 1:1 to about 1:5 parts by weight.

In an embodiment of the present invention, formula I and sulfuric acid is present in an amount from about 1:1 to about 1:3 parts by weight.

In an embodiment, step (a) is carried out at a temperature in the range of about of 5° C. to about 50° C.

In an embodiment, step (b) is carried out at a temperature in the range of about 5° C. to about 50° C.

In an embodiment, step (c) is carried out in the presence of a base.

In another embodiment the base of step (c) is selected from inorganic or organic base.

In an embodiment, step (c) is performed in an organic solvent.

In an embodiment the solvent is selected from polar or nonpolar organic solvent.

In another embodiment, the solvent is selected from amide solvents, aliphatic or aromatic halogenated solvents or aromatic hydrocarbon solvents.

One or more advantages of the present invention are:
1) Economical and environmentally friendly process for large scale preparation of compound of formula IV.
2) Avoids isolation of shock sensitive compound of Formula II.
3) Considerable reduction in generation of acidic effluent.
4) Time savings in unit operations and process.
5) Lesser amount of sulfuric acid required for the reaction.
6) Lesser amount of ammonia required for neutralization.
7) Ammonium sulfate can be recovered from the aqueous effluent.
8) It provides intermediate and final compound in high yield and purity.

The above advantages and other parameters of the present invention is illustrated by the below given examples. However, it should be understood that the scope of the present invention is not limited by the examples in any manner. It will be appreciated by any person skilled in this art that the present invention includes aforesaid examples and further can be modified and altered within the technical scope of the present invention.

EXAMPLES

Example 1: One Pot Process for Preparation of Compound of Formula IV According to the Present Invention 225 g (2.2 moles) of sulfuric acid (98%) was taken in a reaction flask and cooled to 5° C. 140 g (1.11 moles) of guanidine nitrate (97%) was added. The reaction mass was stirred at room temperature for 6-8 hours. The reaction mass was then quenched by the addition of 180 g of water. 265 g of aqueous ammonia (22%) was added to the reaction mass followed by the addition of 69 g (1.13 moles) of ethylene diamine and the reaction mass was heated to 45° C. stirred at the same temperature for 12 hours. The mass was then cooled, neutralized, filtered and then washed with water and dried to get 105 g (70%) of compound of Formula IV (purity –96% (w/w). The final compound of formula IV obtained by this process contained about 0.5% w/w of nitro-guanidine (formula II).

Example 2: Comparison of Two-Step Process for the Preparation of Compound of Formula IV with One Pot Process According to the Present Invention a) Two-step process according to CN107445897
Step 1: Preparation of Compound of Formula II 450 g of concentrated sulfuric acid was taken in a reaction flask and 244 g of compound of Formula I was added. The reaction was stirred at 40° C. for 1 hour. The reaction mass was then cooled to 15~20° C. and quenched by the addition of 4000 g of water. It was then filtered, washed with water, to give 374 g of compound of Formula II.

TABLE 1

| Formula I (g) | $H_2SO_4$ (g) | Water for quenching (g) | Water for washing (g) | Effluent (g) | Formula II (g) |
|---|---|---|---|---|---|
| 244 | 450 | 4000 | 1000 | 5320 | 374 |

Step 2: Preparation of Compound of Formula IV 374 g of compound of Formula II was taken in a reaction flask and 68.6 g of sulfuric acid was added followed by addition of 1055 g of water. 116.3 g of ethylenediamine was then added dropwise and the reaction was warmed to 80~90° C. and stirred for 1 hour. The mass was then cooled, neutralized, filtered and then washed with water and dried to obtain 162 g of compound of Formula IV.

TABLE 2

| Formula II (g) | Ethylene diamine (g) | $H_2SO_4$ (g) | Water for reaction (g) | Water for washing (g) | Effluent (g) | Formula IV (g) |
|---|---|---|---|---|---|---|
| 374 | 116.3 | 68.6 | 1055 | 265 | 1717 | 162 |

Total $H_2SO_4$—518.60 g
Total effluent generated after step 1 and step 2—7037.0 g
Overall yield of the product (step I and II)—62%, (purity 96%)

b) One Pot Preparation of Compound of Formula IV According to the Present Invention 396 g of sulfuric acid was taken in a reaction flask and cooled to 5° C. 244 g of compound of Formula I was added. The reaction mass was stirred at room temperature for 6-8 hours. The reaction mass was then quenched by the addition of 350 of water. 445 g of aqueous ammonia (22%) was added to the reaction mass followed by the addition of 120 g of ethylene diamine and the reaction mass was heated to 45° C., stirred at the same temperature for 12 hours. The mass was then cooled, neutralized, filtered and then washed with water (680 g) and dried to get 182 g of compound of Formula IV. (Yield 70% and purity 96%). The final compound of formula IV obtained by this process contained about 0.5% w/w of nitro-guanidine (formula II).

TABLE 3

| Formula I (g) | $H_2SO_4$ (g) | Water for quenching (g) | Ethylene diamine (g) | ammonia solution (g) | Water for washing (g) | Effluent (g) | Formula IV |
|---|---|---|---|---|---|---|---|
| 244 | 396 | 350 | 120 | 445 | 680 | 2053 | 182 |

The results of various process advantages of one pot process according to the present invention are summarized in the below table (Table 4).

TABLE 4

Comparison of results of two-step process for the preparation of compound of formula IV with one pot process according to the present invention

| Process | $H_2SO_4$ consumed (g) | % Reduction of $H_2SO_4$ | effluent generated (g) | % Reduction of effluent | Yield (%) | Purity (w/w) |
|---|---|---|---|---|---|---|
| Two step process | 518.6 | 23.6 | 7037.0 | 70.8 | 62 | 96 |
| One Pot process | 396.0 | | 2053.0 | | 70 | 96 |

From the above experiments it is demonstrated that there is considerable reduction in the amount of effluent generated as well as the requirement of sulfuric acid. It is also evident that when the reaction is performed in a commercial scale, there can be a vast difference in the amount of effluent generated and thereby the disposal concerns can be addressed more effectively.

Example 3: Preparation of Imidacloprid

Step 1: Preparation of Compound of Formula IV
225 g (2.2 moles) of sulfuric acid (98%) was taken in a reaction flask and cooled to 5° C. 140 g (1.11 moles) of guanidine nitrate (97%) was added. The reaction mass was stirred at room temperature for 6-8 hours. The reaction mass was then quenched by the addition of 180 g of water. 265 g of aqueous ammonia (22%) was added to the reaction mass followed by the addition of 69 g (1.13 moles) of ethylene diamine and the reaction mass was heated to 45° C. stirred at the same temperature for 12 hours. The mass was then cooled, neutralized, filtered and then washed with water and dried to get 105 g (70%) of compound of Formula IV (purity –96% (w/w). It was found that the compound of formula IV (NII) obtained by this process contained about 0.27% of the compound of formula II.

Step 2: Preparation of Imidacloprid

Dimethyl formamide (22.50 ml), compound of Formula IV (39.8 g), K2CO3 (25.5 g) and triethyl benzyl ammonium chloride (0.22 g) at room temperature were charged into a reactor. The mixture was heated to 40° C. A solution of 2-chloro-5-(chloromethyl)pyridine (24.3 g) in dimethyl formamide (13 g) was added to the reaction mixture at 40° C. in 2-3 hours. The reaction mass was then stirred for 6-8 hours at 35 to 40° C., cooled to 30° C. and filtered. The solid was washed with dimethyl formamide (30 ml). Acetic acid (0.8 ml) was added to the filtrate and stirred for 0.5 hr. It was then concentrated and dried to get crude Imidacloprid. This crude imidacloprid was analyzed and found to contain less than or about 0.1% w/w of the compound of formula II. Crude Imidacloprid purified using water to get pure Imidacloprid (31 g). 80.5% yield and purity 97%. This pure imidacloprid was analyzed and found to contain less than or about 0.1% w/w of the compound of formula II. It was also found that the imidacloprid obtained by this process contained about 0.5% w/w of 2-nitroimino imidazolidine.

Example 4: One Pot Process for Preparation of Compound of Formula VI 49 g (0.5 moles) of sulfuric acid (98%) was taken in a reaction flask and cooled to 5° C. 30.5 g (0.25 moles) of guanidine nitrate (97%) was added. The reaction mass was stirred at room temperature for 6-8 hours. The reaction mass was then quenched by the addition of 40 g of water. 58 g of aqueous ammonia (22%) was added to the reaction mass followed by the addition of 18.5 g (0.25 moles) of 1,3-diaminopropane and the reaction mass was heated to 55° C. stirred at the same temperature for 12 to 16 hours. The mass was then cooled, neutralized, filtered and then washed with water and dried to get 24.5 g (68%) of compound of Formula VI.

The invention claimed is:

1. A process for preparation of a nitroimino heterocyclic compound of Formula B:

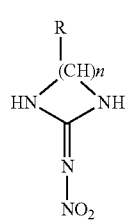

Formula B comprising reacting a compound of Formula II;

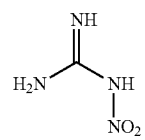

Formula II with a compound of Formula III

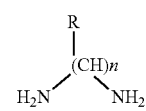

Formula III wherein R represents hydrogen or an optionally substituted lower alkyl of 1 to 4 carbon atoms; and n is 2, 3 or 4;

wherein said compound of formula II is reacted with said compound of formula III without isolating or separating the compound of formula II from a mixture comprising the reaction product of a reaction of a compound of formula I with an acid

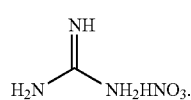

Formula I

2. The process as claimed in claim 1, wherein said nitroimino heterocyclic compound of Formula B is prepared using a diamine of Formula III wherein n is 2.

3. The process as claimed in claim 1, wherein said nitroimino heterocyclic compound of Formula B is prepared using a diamine of Formula III wherein n is 3.

4. The process as claimed in claim 1, wherein said compound of formula B is selected from

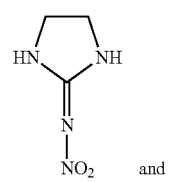

Formula IV and

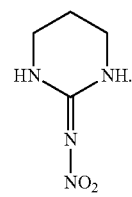

Formula VI

5. The process as claimed in claim 1, wherein said acid is sulfuric acid.

6. The process as claimed in claim 1, wherein the reaction proceeds without isolation of the compound of Formula II.

7. The process as claimed in claim 1, wherein the reaction is carried out at a temperature in the range of about of 5° C. to about 50° C.

8. A one pot process for preparing a nitroimino heterocyclic compound of Formula B

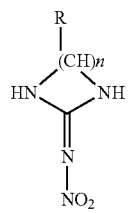

Formula B comprising:

a) reacting a compound of Formula I with an acid to form a compound of Formula II; and

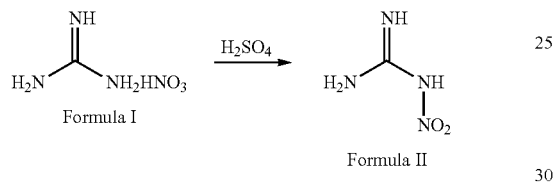

b) reacting compound of Formula II with a compound of Formula III to give a compound of Formula B, wherein compound of formula II is not isolated,

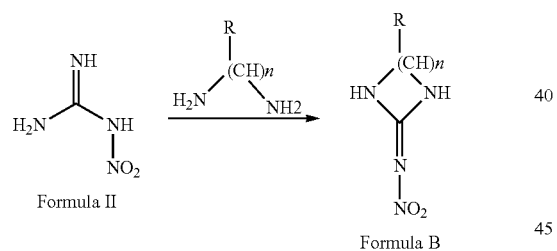

and wherein R represents hydrogen or an optionally substituted lower alkyl of 1 to 4 carbon atoms and n is 2, 3 or 4.

9. The process as claimed in claim 6, wherein said nitroimino heterocyclic compounds of Formula B is a compound of formula IV

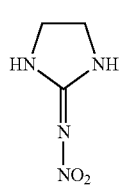

Formula IV

10. A process for preparing a nitroimino heterocyclic compound of Formula IV:

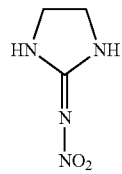

Formula IV said process comprising reacting a compound of Formula II with ethylene diamine to obtain a compound of formula IV:

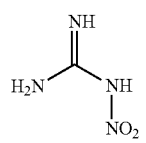

Formula II wherein said compound of formula II is reacted with ethylene diamine without isolating or separating the compound of formula II from a mixture comprising the reaction product of a reaction of a compound of formula I with an acid:

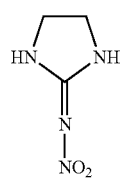

Formula I

11. A one pot process for preparing compound of Formula IV,

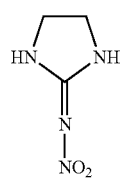

Formula IV comprising:

a) treating a compound of Formula I with sulfuric acid to form a compound of Formula II; and

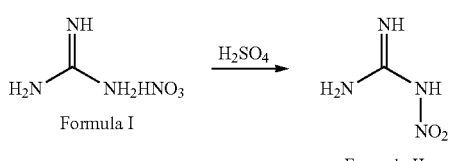

b) treating a compound of Formula II with ethylene diamine to give a compound of Formula IV, wherein compound of Formula II is not isolated

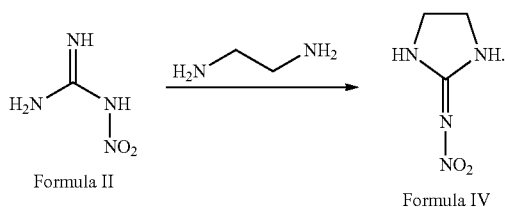
12. The process of claim 4, further comprising reacting the compound of Formula IV with a compound of Formula V to obtain imidacloprid;
13. The process of claim 10, further comprising reacting the compound of Formula IV with a compound of Formula V to obtain imidacloprid;
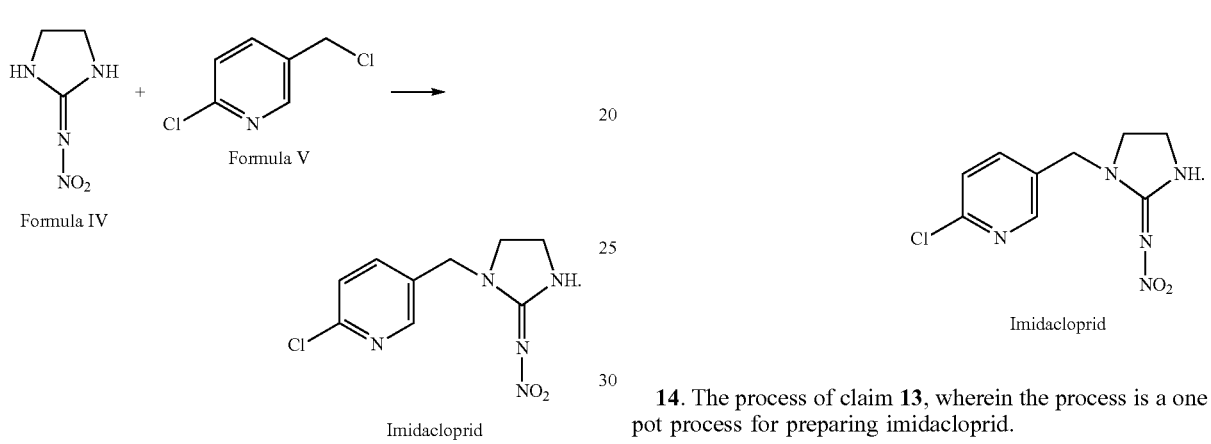
14. The process of claim 13, wherein the process is a one pot process for preparing imidacloprid.
* * * * *